(12) United States Patent
Seifert et al.

(10) Patent No.: US 8,494,656 B2
(45) Date of Patent: Jul. 23, 2013

(54) MEDICAL ELECTRICAL LEADS AND CONDUCTOR ASSEMBLIES THEREOF

(75) Inventors: Kevin R. Seifert, Forest Lake, MN (US); Greg A. Boser, Richfield, MN (US); Mark T. Marshall, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1148 days.

(21) Appl. No.: 12/234,466

(22) Filed: Sep. 19, 2008

(65) Prior Publication Data
US 2009/0082655 A1 Mar. 26, 2009

Related U.S. Application Data

(60) Provisional application No. 60/973,897, filed on Sep. 20, 2007.

(51) Int. Cl.
*A61N 1/375* (2006.01)
(52) U.S. Cl.
USPC .......................................................... 607/122
(58) Field of Classification Search
USPC .................................................. 607/122, 123
See application file for complete search history.

(56) References Cited

U.S. PATENT DOCUMENTS

| | | | |
|---|---|---|---|
| 3,715,458 A * | 2/1973 | Bayes et al. ............... 174/113 R |
| 4,443,657 A | 4/1984 | Hill et al. |
| 4,467,138 A | 8/1984 | Brorein |
| 4,523,086 A | 6/1985 | Eilentropp |
| 4,564,723 A | 1/1986 | Lang |
| 4,650,924 A | 3/1987 | Kauffman et al. |
| 4,719,319 A | 1/1988 | Tighe, Jr. |
| 4,861,945 A | 8/1989 | Buck et al. |
| 4,952,020 A | 8/1990 | Huber |
| 4,972,041 A | 11/1990 | Crawley et al. |
| 5,053,583 A | 10/1991 | Miller et al. |
| 5,209,987 A | 5/1993 | Penneck et al. |
| 5,245,134 A | 9/1993 | Vana, Jr. et al. |
| 5,262,589 A | 11/1993 | Kesler |
| 5,483,022 A | 1/1996 | Mar |
| 6,456,888 B1 * | 9/2002 | Skinner et al. ................ 607/116 |
| 6,650,921 B2 | 11/2003 | Spehr et al. |

(Continued)

OTHER PUBLICATIONS

PCT/US2008/077099, Partial International Search, dated Apr. 7, 2009, 2 pages.

(Continued)

*Primary Examiner* — Kennedy Schaetzle
*Assistant Examiner* — Erica Lee
(74) *Attorney, Agent, or Firm* — Reed A. Duthler; Stephen W. Bauer

(57) ABSTRACT

A conductor assembly for a medical electrical lead includes a web and plurality of conductors. The web includes a plurality of longitudinally extending elements, or sidewalls, each of which define a longitudinally extending lumen, and a plurality of longitudinally extending connectors, each of which join a pair of adjacent sidewalls. Each of the plurality of conductors extends within a corresponding lumen, and each may include an insulative jacket. If each conductor includes an insulative jacket, the jacket is preferably formed from one or more of the following materials: PEEK, PVDF and polysulfone. One or more of the connectors of the web may be flexible to allow for a connected separation, or a gap between adjacent sidewalls; and one or more of these connectors may further include a discrete wall section adapted to facilitate widening of the corresponding gap. Preferably the conductor assembly is coiled for incorporation into the lead.

4 Claims, 7 Drawing Sheets

U.S. PATENT DOCUMENTS

| | | |
|---|---|---|
| 6,671,554 B2 | 12/2003 | Gibson et al. |
| 6,766,578 B1 | 7/2004 | Swanson et al. |
| 6,855,889 B2 | 2/2005 | Gareis |
| 6,984,789 B2 | 1/2006 | Glaser et al. |
| 7,239,923 B1 * | 7/2007 | Tockman et al. ............. 607/119 |
| 7,271,340 B2 | 9/2007 | Buck et al. |
| 2003/0092303 A1 | 5/2003 | Osypka |
| 2003/0195602 A1 * | 10/2003 | Boling .......................... 607/122 |
| 2005/0016657 A1 | 1/2005 | Bluger |
| 2005/0246007 A1 * | 11/2005 | Sommer et al. ............... 607/127 |
| 2006/0293737 A1 * | 12/2006 | Krishnan ...................... 607/122 |
| 2007/0250143 A1 | 10/2007 | Sommer |

OTHER PUBLICATIONS

PCT/US2008/077099, International Search Report and Written Opinion, dated Jul. 3, 2009, 16 pages.

* cited by examiner

MEDICAL ELECTRICAL LEADS AND CONDUCTOR ASSEMBLIES THEREOF

CROSS-REFERENCE TO RELATED APPLICATION

The present application claims priority and other benefits from U.S. Provisional Patent Application Ser. No. 60/973,897, which was filed on Sep. 20, 2007, and which is incorporated herein by reference in its entirety.

TECHNICAL FIELD

The invention relates to implantable medical devices and, more particularly, to implantable medical leads.

BACKGROUND

An implantable medical electrical lead that provides, for example, diagnostic sensing within a body of a patient and/or electrical stimulation pulses to tissue of the patient, typically includes a flexible elongate body formed, at least in part, by an assembly of elongate conductors. Each conductor electrically couples a sensing electrode, a stimulation electrode, or a sensor of the lead, to a connector of the lead. The connector couples the lead to a device that includes a power source and electronic circuitry. Each conductor of the lead typically includes at least one conductive wire surrounded by a layer of insulation to electrically isolate one conductor from another and/or to isolate each conductor from the operating environment of the lead, for example, within the body of the patient. Although various configurations of conductor assemblies for implantable medical electrical leads have been disclosed in the past, there is still a need for new conductor assemblies.

BRIEF DESCRIPTION OF THE DRAWINGS

The following drawings are illustrative of particular embodiments and therefore do not limit the scope of the invention. The drawings are not to scale (unless so stated) and are intended for use in conjunction with the explanations in the following detailed description. Embodiments of the present disclosure will hereinafter be described in conjunction with the appended drawings, wherein like numerals denote like elements and wherein.

DETAILED DESCRIPTION

The following description is merely exemplary in nature and is not intended to limit the present disclosure, application or uses. One will understand that the components, including number and kind, may be varied without altering the scope of the disclosure. Additionally, devices according to various embodiments may be used in any appropriate diagnostic or treatment procedure, including a cardiac or neural procedure.

Figure 1:
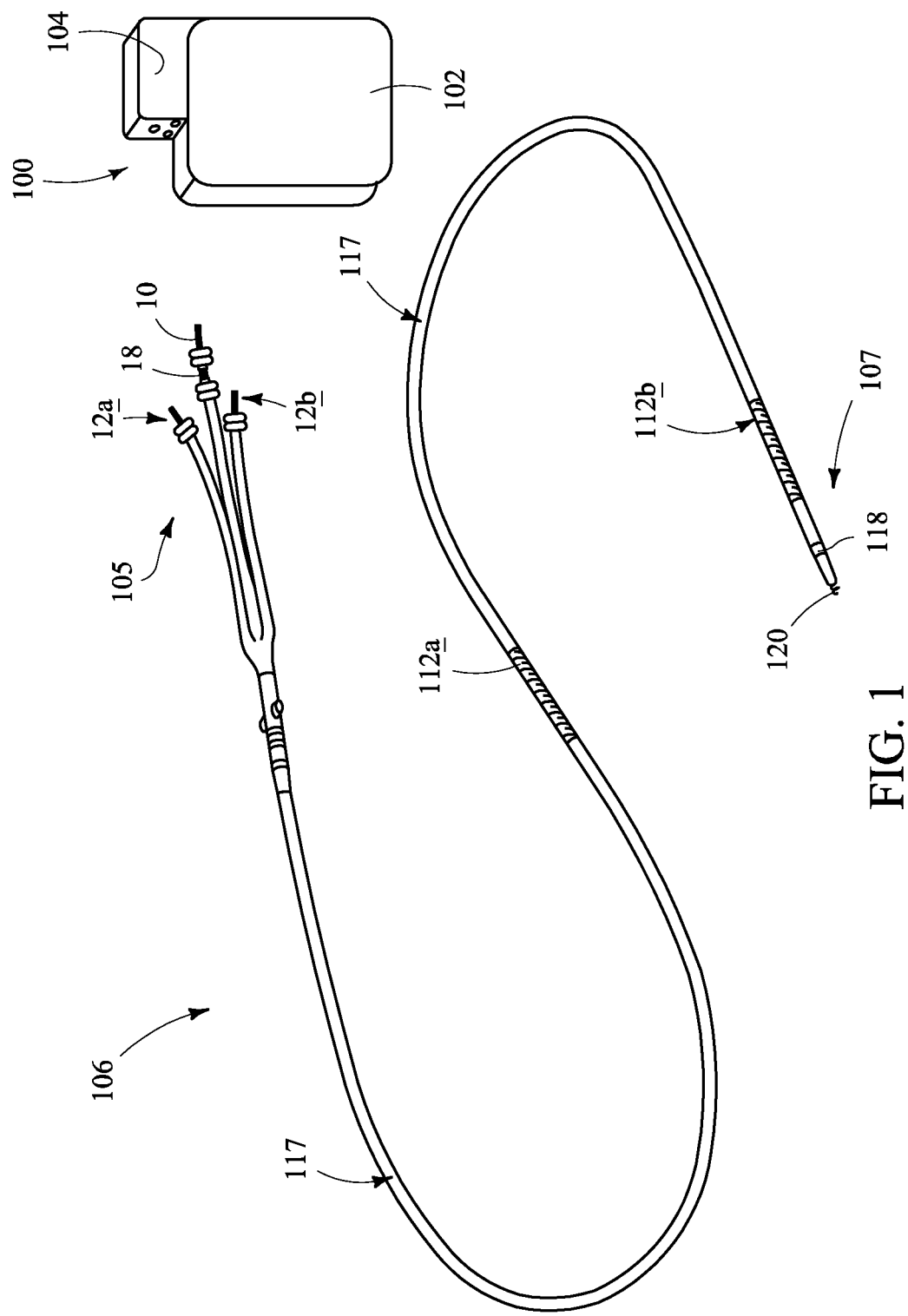
FIG. 1 is a schematic of a system that includes an implantable medical device and an implantable medical electrical lead, which lead may incorporate embodiments of the present invention.
Figure 2:
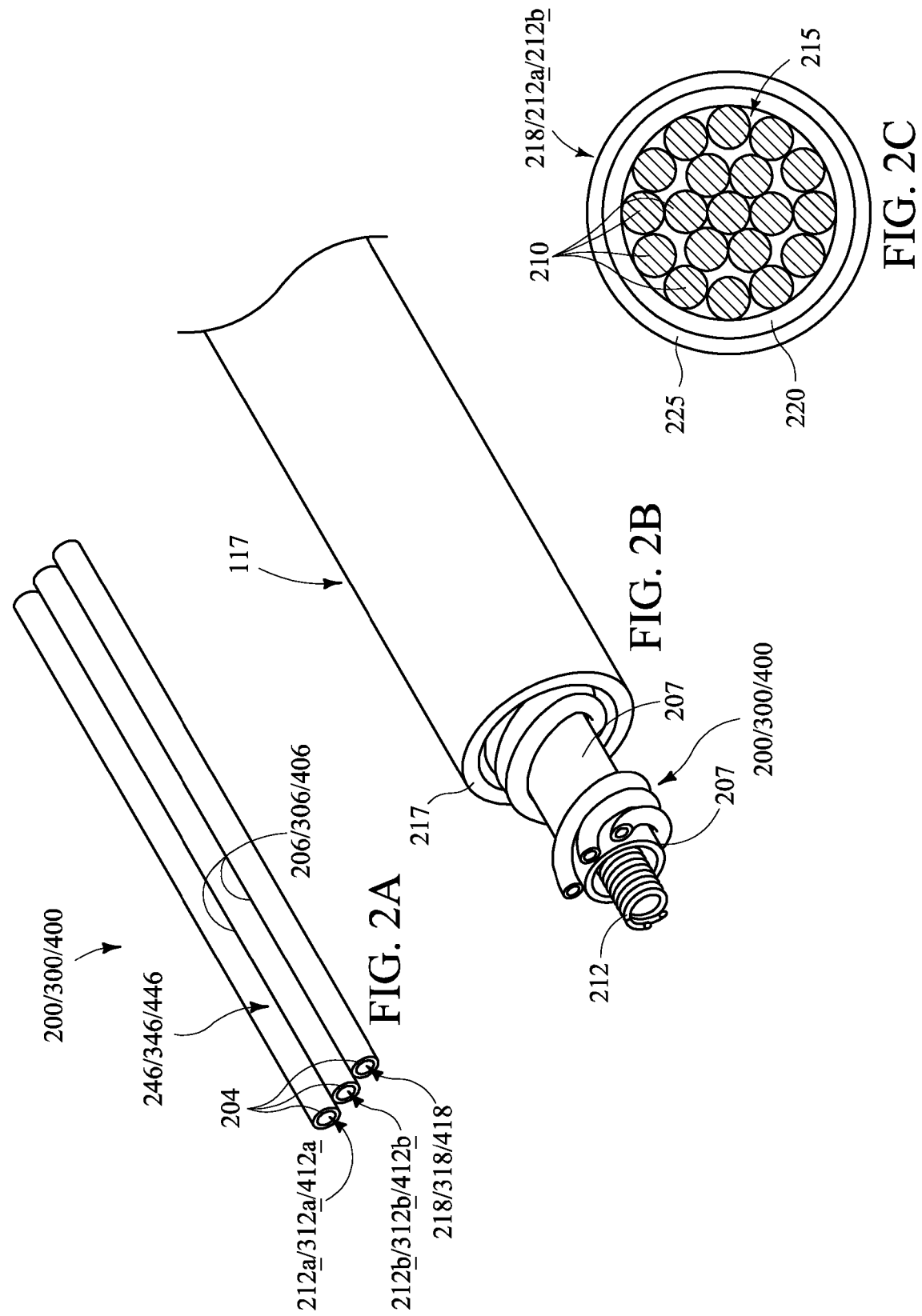
FIG. 2A is a perspective view of a conductor assembly, generally representing various embodiments of the present invention.
FIG. 2B is an exploded section view, per section line A-A of FIG. 1, wherein the conductor assembly of FIG. 2A is incorporated, according to some embodiments of the present invention.
FIG. 2C is a cross-section of a conductor, which may be included in conductor assemblies of the present invention, according to some embodiments.

FIG. 1 is a schematic of a system including an implantable medical device 100 and an implantable medical electrical lead 106, which lead 106 may incorporate embodiments of the present invention. FIG. 1 illustrates lead 106 including a lead body 117, which extends from a proximal end 105 to a distal end 107, and to which electrodes 112a, 112b, 118 and 120 are attached. FIG. 1 further illustrates device 100 including a can, or housing 102 to which a header, or connector module 104 is attached. Although not seen in FIG. 1, it should be appreciated that a conductor corresponding to each electrode 112a, 112b, 118, 120 of lead 106 electrically couples each electrode 112a, 112b, 118, and 120 to a corresponding connector contact 12a, 12b, 18 and 10, respectively, which are each attached to connector legs terminating proximal end 105 of lead body 117. Those skilled in the art will further appreciate that each of the connector legs of lead 106 may be plugged into corresponding ports of connector module 104 of device 100, wherein electrical contacts, that correspond to each of connector contacts 12a, 12b, 18, 10, are mounted; the electrical contacts of each port are coupled via a feedthrough assembly to a power source and electronic circuitry which is hermetically sealed within housing 102 of device 100. Although the illustrated proximal end 105 includes multiple connector legs, which may each conform to an appropriate industry standard for lead connectors, proximal end 105 may, alternately, include a single connector leg, for example, one on which all of contacts 12a, 12b, 18 and 10 are mounted, and one which, likewise, may conform to an appropriate industry standard. According to embodiments of the present invention, a lead body subassembly composed of an assembly of the aforementioned conductors, which extend within lead body 106, are connected together by a web, for example, in a ribbon-like fashion as shown in FIG. 2A. It should be noted that, although FIG. 1 illustrates a system suited for delivery of cardiac defibrillation therapy, wherein electrodes 12a and 12b are adapted to deliver defibrillation shocks, and electrodes 18 and 10 are adapted for pacing and sensing, embodiments of the present invention are not limited to a therapy delivery system (for example, embodiments could be implemented in a solely diagnostic system that includes one or more sensors, for example, pressure, oxygen, electrical, etc.), or to any particular type of therapy delivery or diagnostic system, or combination thereof.

Figure 3:
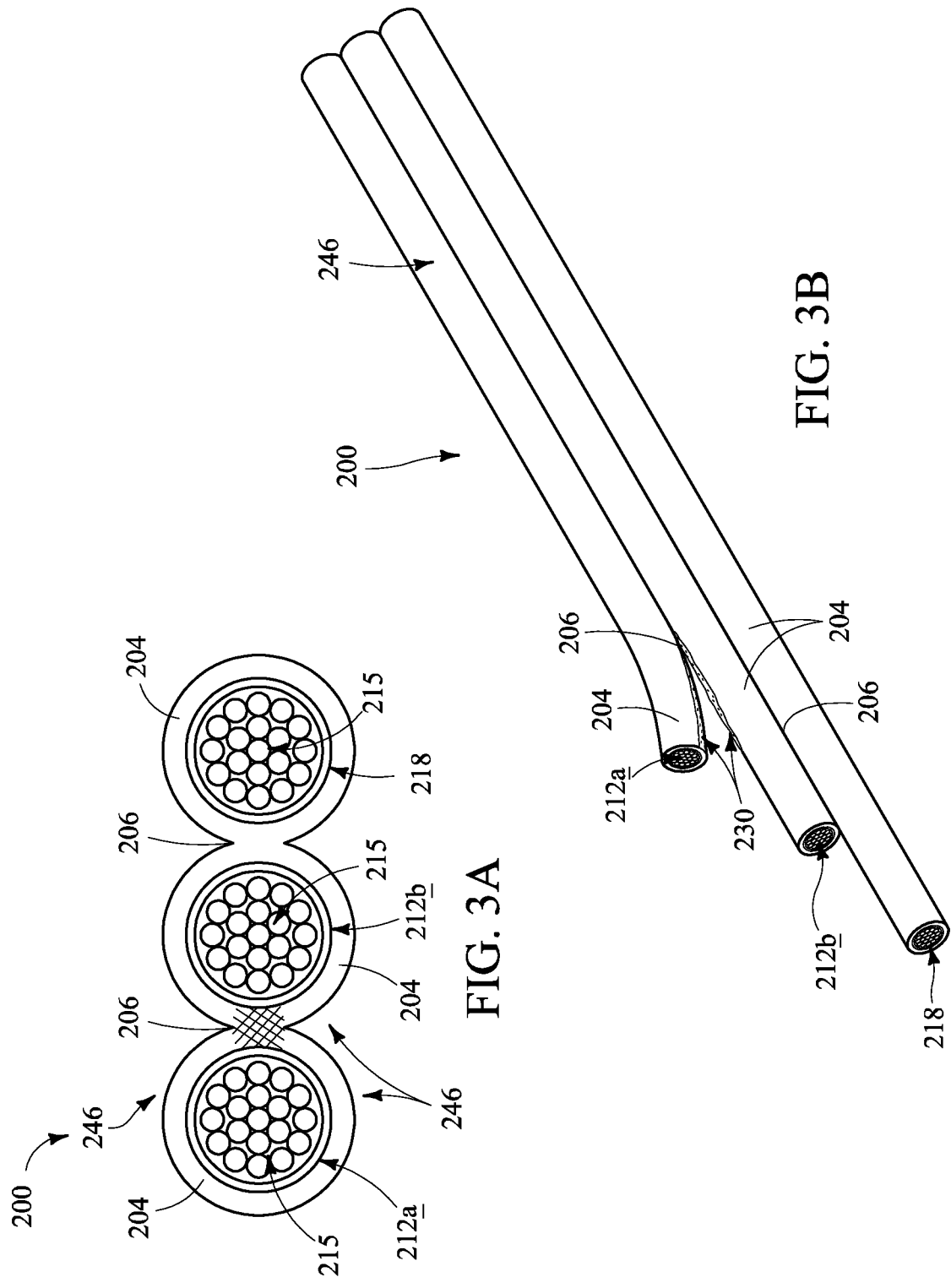
FIGS. 3A, 4A and 5A are cross-sections, per section line B-B of FIG. 2A, according to the various embodiments of the conductor assembly.
FIGS. 3B, 4B and 5B are schematics corresponding to FIGS. 3A, 4A and 5A, respectively, which depict a separation of one conductor of each assembly from the rest of the conductors of the corresponding assembly, according to some embodiments.
Figure 4:
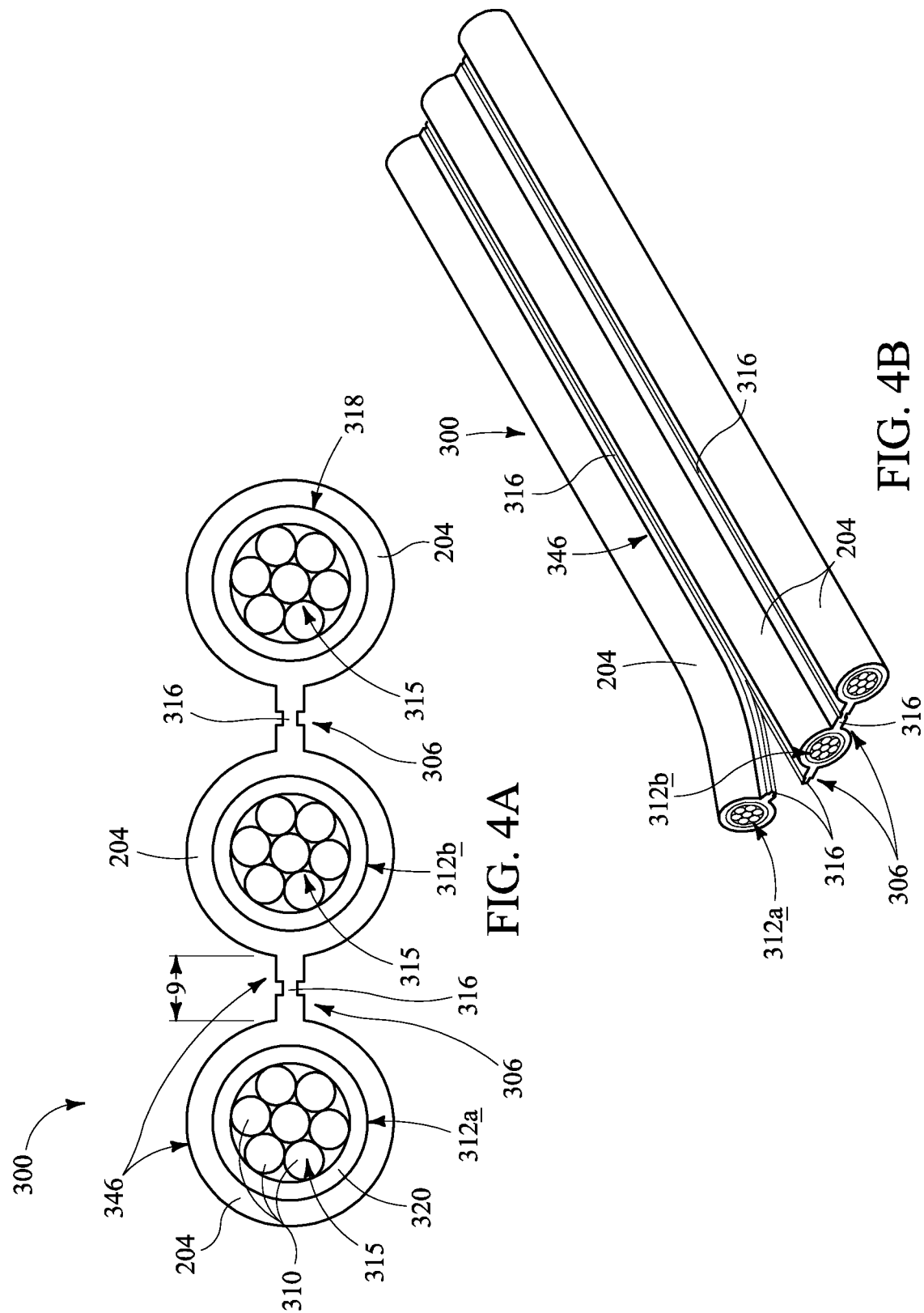
Figure 5:
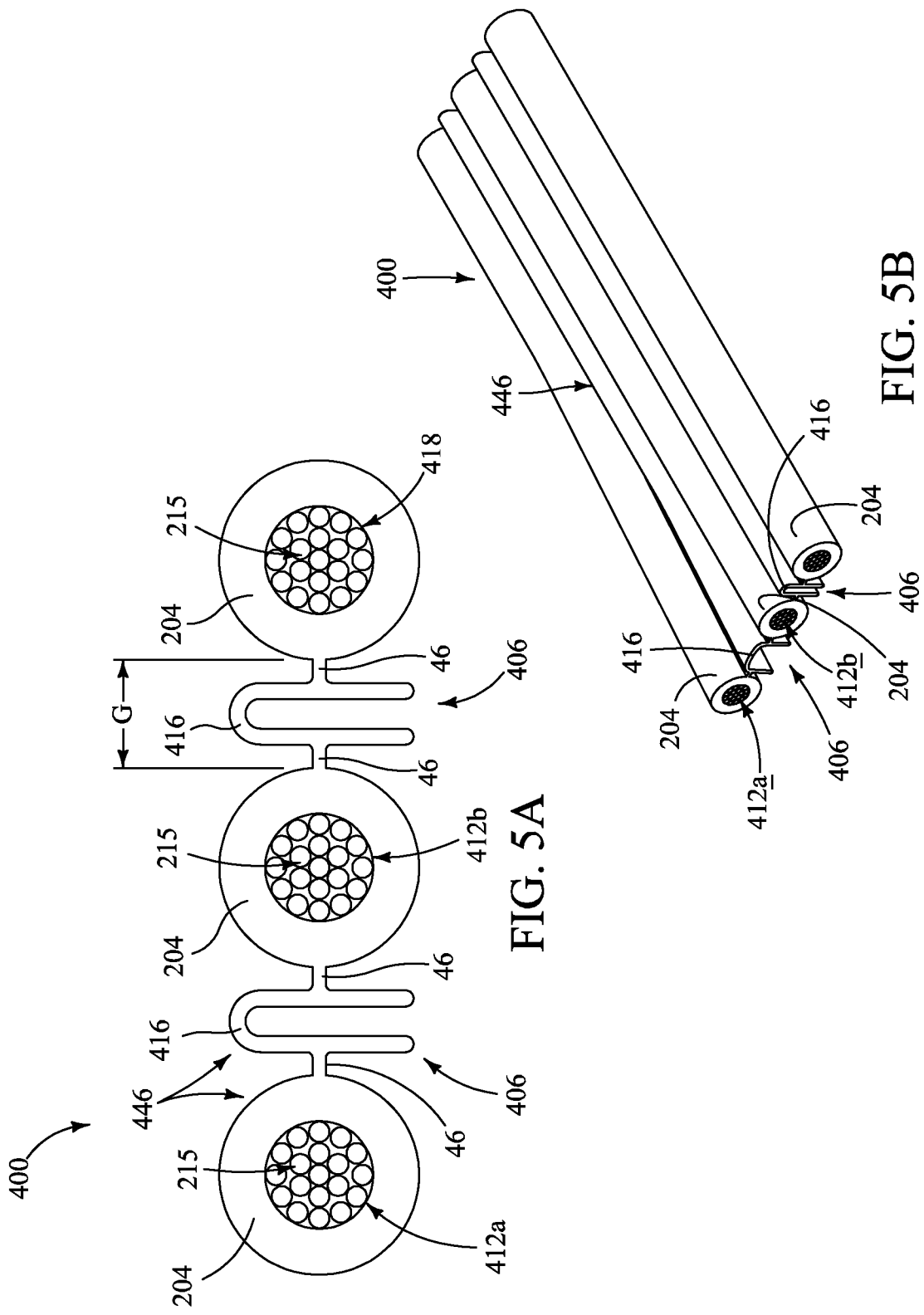

FIG. 2A is a perspective view of a lead body subassembly, or conductor assembly 200/300/400, generally representing various embodiments of the present invention, which are shown in cross-section, per section line B-B, in FIGS. 3A, 4A and 5A as assemblies 200, 300 and 400, respectively. FIG. 2A illustrates conductor assembly 200/300/400 including an insulative web 246/346/446 that connects conductors 212a/312a/412a, 212b/312b/412b and 218/318/418 together; web 246/346/446 is shown including a plurality of longitudinally extending elements, or sidewalls 204, which each form a lumen within which the corresponding conductor extends, and a plurality of longitudinally extending connectors 206/306/406, which each join a pair of adjacent sidewalls 204. According to preferred embodiments, sidewalls 204 and connectors 206/306/406 are flexible, for example, to allow coiling of conductor assembly 200/300/400 within lead body 117, for example as shown in FIG. 2B, which is an exploded section view, through section line A-A of FIG. 1.

According to the illustrated embodiment, each conductor 212a/312a/412a, 212b/312b/412b, 218/318/418 of conductor assembly 200/300/400 couples the corresponding electrode 112a, 112b, 118 to the corresponding connector contact 12a, 12b, 18, and conductor assembly 200/300/400 extends within an outer insulative sheath 217, of lead body 117 and is coiled about an inner insulative sheath 207 of lead body 117, in which another conductor 212 extends to couple electrode 120 to connector contact 10. Assembly 200/300/400 may be coiled about a mandrel and heat set into the coiled configuration, prior assembling assembly 200/300/400 into lead body 117. Outer and inner sheaths 217, 207 may formed from medical grade polyurethane or silicone, or a combination thereof. According to some preferred embodiments, each of conductors 212a/312a/412a, 212b/312b/412b, 218/318/418 is made up of a cabled bundle of wire strands, for example, each formed from MP35N alloy, either solid or silver-cored. Alternately, each, or any, of conductors 212a/312a/412a, 212b/312b/412b, 218/318/418 may be formed as a solid, single wire, a coaxial combination in which a solid insulated wire is surrounded by one or more coiled wire filars, or a coaxial combination in which an insulated cable is surrounded by one or more coiled wire filars.

FIG. 2C is a cross-section of a type of conductor 218/212a/212b, according to some embodiments, which is shown included in conductor assembly 200 of FIG. 3A as conductors 218, 212a and 212b. FIG. 2C illustrates conductor 218/212a/212b including a cable 215 made up of a plurality of wire strands 210, for example, each having a diameter between approximately 0.0005 inch and approximately 0.005 inch; strands 210 may be stranded with a pitch between approximately 0.03 inch and approximately 0.06 inch into what is known to those skilled in the art as a 1×19 configuration. Another exemplary cable 315 is illustrated in FIG. 4A according to a 7×7 configuration, wherein each of elements 310 includes a cabled bundle of seven wire strands; such a configuration is described in commonly-assigned U.S. Pat. No. 5,760,341, which is hereby incorporated by reference. Another exemplary cable may have a 1×7 configuration comprised of wire strands having diameters between approximately 0.004 inch and approximately 0.005 inch, with a pitch between approximately 0.040 inch and approximately 0.070 inch. Although MP35N alloy is commonly employed for conductor cables, used in implantable medical electrical leads, embodiments of the present invention may alternately employ cables formed from any other suitable biostable and biocompatible material that is sufficiently resistant to flex fatigue; some examples of alternative materials include, without limitation, stainless steel, tantalum, tantalum alloys, titanium, titanium alloys, either solid or cored.

FIG. 2C further illustrates conductor 218/212a/212b including an insulative jacket, which is formed by a first insulation layer 220 and an optional second insulation layer 225; it should be noted that any number of insulative layers may be employed by conductors in assemblies of the present invention. Either or both of layers 220, 225 of the insulative jacket may be co-extruded over cable 215; alternately either or both of layers 220, 225 may be formed by a coating process; suitable methods for forming insulative jackets depend, at least in part, upon the material selected for the jackets. Suitable materials for either of layers 220, 225 of the jacket include, without limitation, fluoropolymers, such as PTFE; thermoplastic fluoropolymers, such as ETFE, polyvinylidene difluoride (PVDF), fluorinated ethylene propylene (FEP), perfluoroalkoxy copolymer (PFA), and terpolymer of tetrafluoroethylene, hexafluoropropylene and vinylidene fluoride (THV), for example, Dyneon™ THV, available from 3M; flouroelastomers, such as DAI-EL T530, available from Daikin, and blends of DAI-EL T530, such as with ETFE; an adhesive fluoropolymer, such as ethylene perfluoro-ethylene propene EFEP (i.e. NEOFLON™, available from Daikin); blends of polyurethanes (PU); polyurethane-silicone copolymers; polyurethanes with surface modifying endgroups (SME); silicones; polyimides, such as Si-soluble Imide; polysulfones; and polyetheretherketones (PEEK). PVDF, polysulfone and PEEK, may be preferred, for either or both of layers 220, 225, due to their relatively high modulus which helps assembly 200 to retain its subsequently coiled shape (FIG. 2B).

Referring now to FIG. 3A, it may be appreciated that sidewalls 204 of web 246 may be co-extruded over each conductor 212a, 212b, 218 individually and then joined to form connectors 206, for example, via a thermal bonding/fusing process. Suitable materials for web 246, formed in this manner, would, preferably, have a lower melting point than the material(s) forming the insulative jacket, i.e. layers 220, 225. Some exemplary suitable material combinations are identified in TABLE 1.

TABLE 1

| Layer 220 | Layer 225 (optional) | Sidewall 204 |
|---|---|---|
| PEEK | — | ETFE |
| PEEK | — | PU |
| PEEK | ETFE | PU |
| PEEK | ETFE | EFEP |
| PEEK | — | EFEP |
| PEEK | — | Silicone |
| PEEK | — | THV (Dyneon) |
| PEEK | — | DAI-EL T530 (Daikin) |
| PVDF | — | PU |
| Polyimide | — | ETFE |
| Polyimide | — | PU |
| SI-soluble Imide | — | ETFE |
| SI-soluble Imide | — | PU |

With reference back to FIG. 1, in conjunction with FIGS. 2B and 3B, it may be appreciated that each conductor 212a, 212b, 218 is preferably terminated at the corresponding coupling, or junction with each electrode 112a, 112b, 118, such that each sidewall 204 of web 246 is also terminated in proximity to the termination of the corresponding conductor. Thus, the sidewall 204 that corresponds to conductor 218 extends distally, along a length of lead 106, beyond the sidewall 204 that corresponds to conductor 212b; and the sidewall 204 that corresponds to conductor 212b, likewise extends distally, along a length of lead 106, beyond the sidewall 204 that corresponds to conductor 212a. Although FIG. 3B shows each conductor, and corresponding web sidewall, having been cut to length prior to coiling assembly 200 into the configuration shown in FIG. 2B, it should be noted that the trimming of each conductor to length is alternatively performed after assembly 200 is coiled. In either case, each conductor is separated from the adjacent conductor in proximity to the corresponding junction, and FIG. 3B depicts a separation of conductor 212a from the rest of conductor assembly 200.

With reference to FIGS. 3A-B, it may be appreciated that when adjacent conductors are separated at connectors 206, a breach 230 may be formed in one or both of the web sidewalls 204 that are on either side of the corresponding connector 206 (location for potential breaching shown by cross-hatching in FIG. 3A). According to the illustrated embodiment, breaches 230 of web sidewalls 204 will not compromise the electrical isolation of conductors 212a, 212b, since each conductor includes the insulative jacket as previously described. However, it may still be desirable to eliminate the potential for breaching web sidewalls 204, and alternative web connectors that do so may also significantly increase the flexibility of the corresponding webs, which increased flexibility may further facilitate the forming of conductor assemblies for incorporation within lead bodies, either coiled, as shown in FIG. 2B, or otherwise wrapped or rolled. FIGS. 4A-5B illustrate some such alternate web connector configurations, which may be co-extruded over sets of conductors, for example, to form assemblies 300, 400. For those embodiments, in which the sidewalls of the web serve as a primary insulation, as well as for any other embodiment described herein, it may be preferable that a thickness of each connector be substantially less than that of the sidewalls.

FIGS. 4A-B illustrate conductor assembly 300 including a web 346 and conductors 312a, 312b, 318; web 346 is shown including longitudinally extending sidewalls 204, which each define a lumen, within which a corresponding conductor 312a, 312b, 318 extends. FIGS. 4A-B further illustrate adjacent sidewalls 204 joined together by a longitudinally extending flexible connector 306, which provides a gap g between the connected adjacent sidewalls 204; each connector 306 is also shown including a discrete wall section 315, which extends continuously along a length of the corresponding connector 306. According to the illustrated embodiment, each wall section 315 is formed by notch or a thinned region of the corresponding connector 306 and facilitates a widening of gap g, for example, to separate conductor 312a from adjacent conductor 312b, as shown in FIG. 4B, in order to couple conductor 312a to electrode 112a (FIG. 1).

Since wall sections 316 provide a zone where connectors 306 are weakened, connectors 306 will preferentially split apart at wall sections 316, when the conductors are separated, for example, as shown in FIG. 4B, thereby significantly reducing the potential for breaching sidewalls 204. Thus, although FIG. 4A shows each of conductors 312a, 312b, 318 including an insulative jacket 320, which may be the primary insulation for each cable 315 (previously described), sidewalls 204 may alternately form a primary insulation for each cable 315, and jackets 320 need not be included. Sidewalls 204 of an insulative web 446 of conductor assembly 400, shown in FIGS. 5A-B, serve as such for cables 215. It should be noted that wall sections 316 may extend substantially across gap g and may have a thickness that is substantially less than a thickness of sidewalls 204.

FIGS. 5A-B illustrate conductors 412a, 412b, 418 of conductor assembly 400 formed by cables 215 extending within respective lumens formed by sidewalls 204 of web 446; adjacent sidewalls 204 are joined together by a longitudinally extending flexible connector 406, which, like connectors 306 of assembly 300, provides gap g between the connected adjacent sidewalls 204. Each connector 406 is also shown including a discrete wall section 416, which is formed in a U-shaped fold and extends continuously along a length of the corresponding connector 406, and, according to the illustrated embodiment, facilitates a widening of gap g, for example, to separate conductor 412a from adjacent conductor 412b, as shown in FIG. 5B, in order to couple conductor 412a to electrode 112a (FIG. 1).

Figure 6:
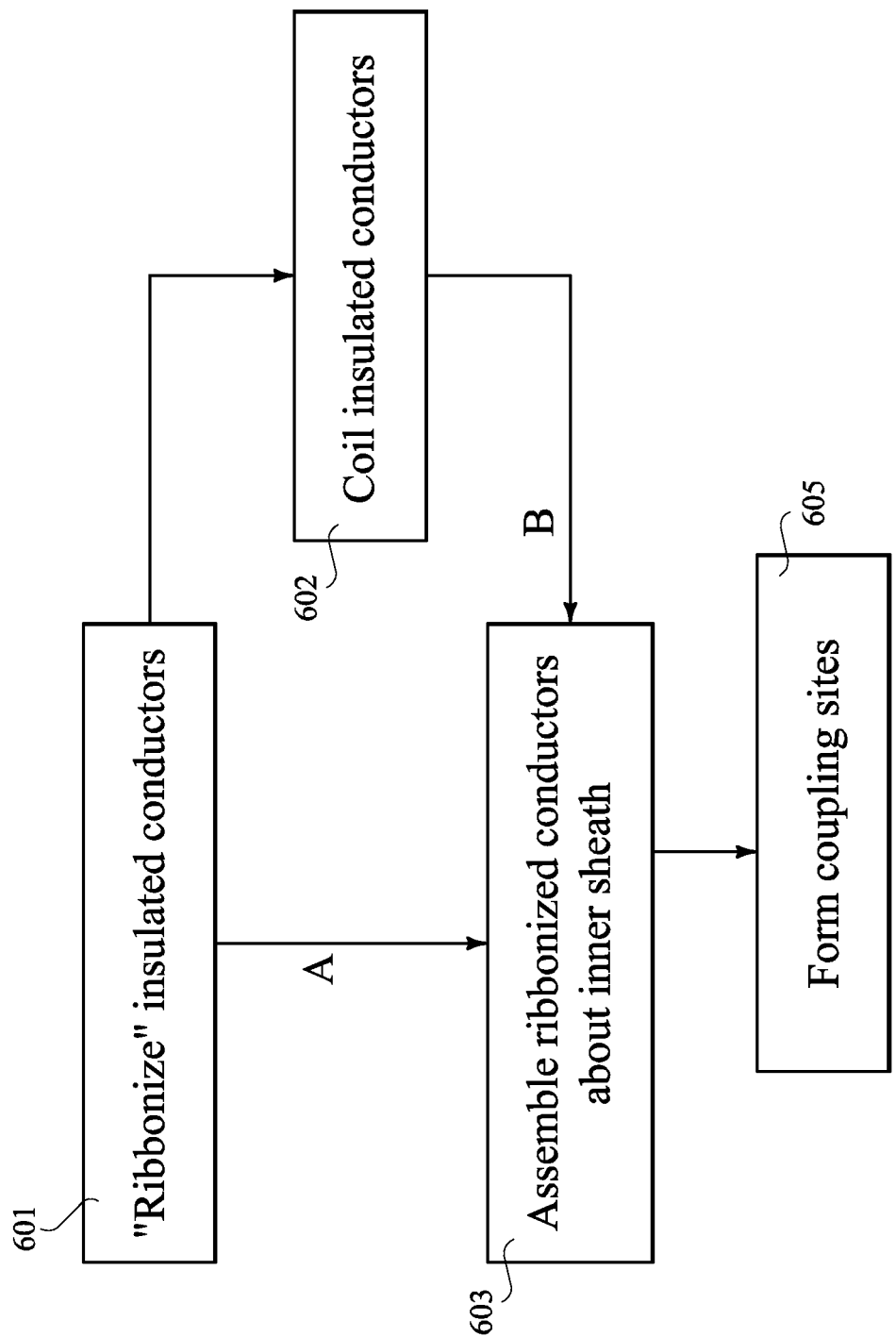
FIG. 6 is a flow chart outlining some methods of the present invention.

FIG. 6 is a flow chart outlining some methods of the invention, for making a lead body subassembly that includes conductor assemblies of the present invention. FIG. 6 illustrates a "ribbonizing" step 601 wherein a plurality of insulated conductors are joined together by a web, for example, similar to any of webs 246, 346, 446 of assemblies 200, 300 and 400, respectively, which are described above. "Ribbonizing" may be performed via a thermal bonding or fusing process, for example, accomplished via a hot air nozzle, wherein at least an outer portion of a jacket of insulation surrounding each of the insulated conductors is adhered to that of each adjacent conductor. Alternately, the web may be co-extruded over the plurality of insulated conductors. Following step 601, per path A, the "ribbonized" conductors are assembled, per step 603, about an insulative sheath, for example, like sheath 207, shown in FIG. 2B; the assembling may be accomplished by wrapping or coiling the conductors about the sheath. Alternately, per path B, the "ribbonized" conductors are coiled, per step 602, prior to assembling about the insulative sheath, per step 603. The coiling, per step 602, preferably includes heat setting, according to methods known in the art, wherein time and temperature parameters depend upon conductor, insulation and web materials. Step 603 may also include heat setting in order to maintain the conformance of the ribbonized conductors about the insulative sheath. Alternately, or in addition, step 603 includes bonding, wherein portions of the ribbonized conductors are adhered to the sheath. In step 605, coupling sites, for electrical connection, are formed for each insulated conductor, for example, by separating each conductor from the adjacent conductors in proximity to the site and then stripping away insulation at the site. The coupling sites may be tailored for any suitable coupling method, known to those skilled in the art, some examples of which include: crimping, swaging and welding. According to some embodiments, step 605 further includes trimming, or cutting to length, one or more of the insulated conductors and associated web sidewall, wherein the coupling site is formed at the trimmed end. This trimming serves to stagger the locations of coupling sites, for each of the insulated conductors in the conductor assembly, along a length of the lead body subassembly, as previously described. It should be noted that, the trimming, if necessary, may be performed prior to step 603, according to alternate embodiments. Likewise, the stripping may be performed prior to step 603, such that the entirety of step 605 may be performed prior to step 603.

With further reference to FIG. 6, according to some alternate methods of the present invention, steps 601, 602 and 603 are encompassed by a single process to form a subassembly in which the insulative sheath serves as a the web that connects the insulated conductors together. According to these alternate methods, a set of individual insulated conductors are wound about the sheath such that the conductors are embedded therein and adhered thereto.

Figure 7:
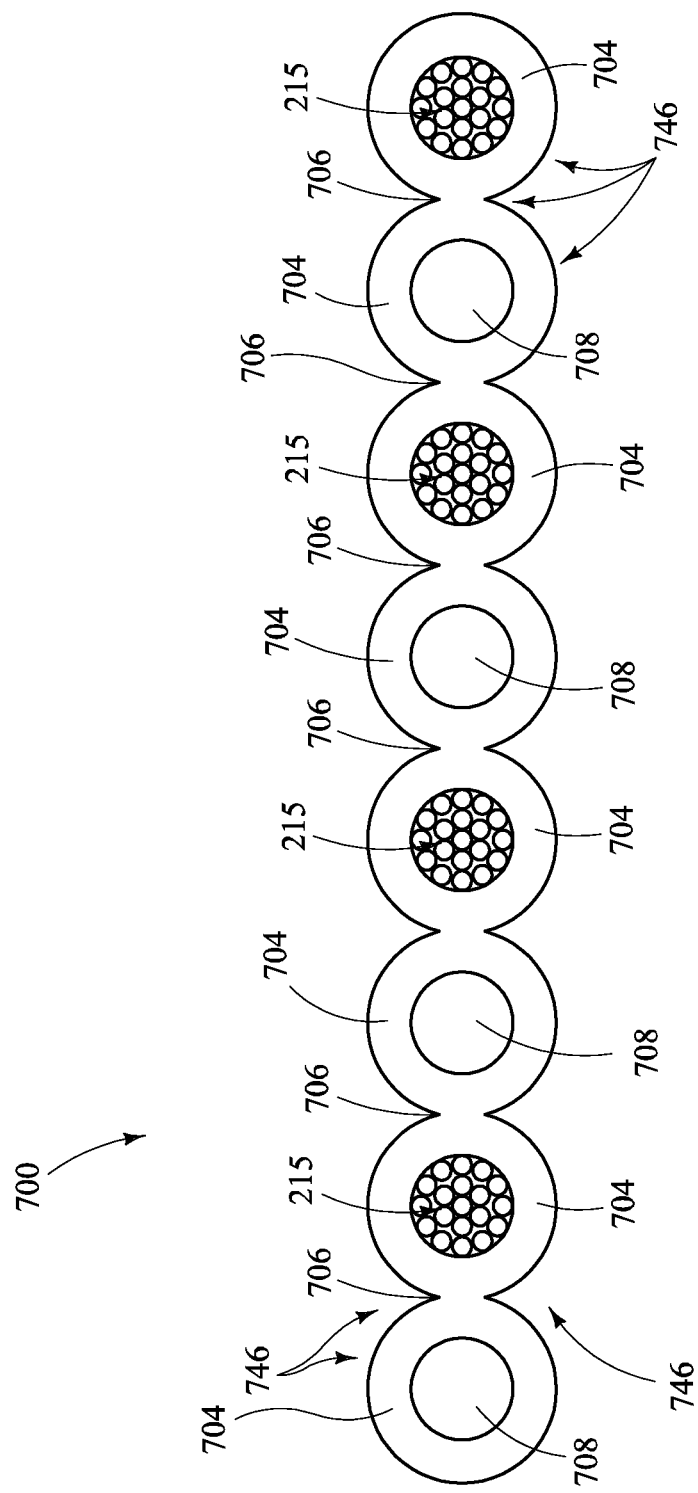
FIG. 7 is a cross-section of a conductor assembly, according to some additional embodiments of the present invention.

FIG. 7 is a cross-section of a conductor assembly 700, according some additional embodiments of the present invention. It should be noted, that although not specifically shown, assembly 700 extends longitudinally in a similar fashion to assemblies 200, 300 and 400. FIG. 7 illustrates an insulative web 746 of assembly 700 including a plurality of sidewalls 704 and a plurality of connectors 706, which join adjacent sidewalls 704 to one another. Each of sidewalls 704 is shown defining a lumen; in some lumens, a conductor, formed by cable 215, extends, while other lumens surround an open space 708. Spaces 708 may serve as conduits for passage therethrough of an elongate member, for example, facilitating lead implant, like a guide wire, or of an injectable medium, for example, a therapeutic or diagnostic agent. Open spaces 708 may be formed by removing mandrels, for example, silver-plated copper mandrels, from within the respective sidewalls 204 after co-extruding web 746 over conductor cables 215 and the mandrels. According to some alternate embodiments, one or more of spaces 708 may be filled with members other than conductors, for example, non-conductive members, that may lend additional strength to assembly 700, and/or provide for additional electrical isolation. Web 746 may be co-extruded over the conductor cables and the other members. It should be noted that, although a particular number of spaces and conductors, and a particular arrangement of spaces with respect to conductors are illustrated in FIG. 7, the scope of the invention is not so limited, and alternate embodiments may including alternate numbers and arrangements of each.

In the foregoing detailed description, the invention has been described with reference to specific embodiments. However, it may be appreciated that various modifications and changes can be made without departing from the scope of the invention as set forth in the appended claims.

We claim:

1. A method for making a lead body subassembly, the method comprising:

assembling a conductor assembly about an insulative sheath, the conductor assembly including a web, a first conductor and a second conductor, the web including a first sidewall that defines a lumen through which the first conductor extends, a second sidewall that defines a lumen through which the second conductor extends, and a connector joining the first sidewall to the second sidewall;

trimming the first sidewall and the first conductor of the conductor assembly, together, such that the first sidewall and the first conductor have a length that is less than a length of the second sidewall and the second conductor;

coiling the conductor assembly prior to assembling the conductor assembly about the insulative sheath; and wherein the trimming is performed between the steps of coiling and assembling.

2. A method according to claim 1, wherein assembling the conductor assembly about the insulative sheath comprises bonding portions of the conductor assembly to the sheath.

3. The method of claim 1, wherein each connector of the web is sufficiently flexible to allow for a gap between connected adjacent sidewalls of the web.

4. The method of claim 1, wherein each conductor is a cable including a plurality of conductive wire strands.

* * * * *